(12) United States Patent
Lachner et al.

(10) Patent No.: US 11,741,614 B2
(45) Date of Patent: *Aug. 29, 2023

(54) METHOD, SYSTEM AND COMPUTER PROGRAM FOR DETERMINING POSITION AND/OR ORIENTATION PARAMETERS OF AN ANATOMICAL STRUCTURE

(71) Applicant: Brainlab AG, Munich (DE)

(72) Inventors: Rainer Lachner, Munich (DE); Katrin Unterlindner, Munich (DE)

(73) Assignee: BRAINLAB AG, Munich (DE)

( * ) Notice: Subject to any disclaimer, the term of this patent is extended or adjusted under 35 U.S.C. 154(b) by 0 days.

This patent is subject to a terminal disclaimer.

(21) Appl. No.: 17/579,245

(22) Filed: Jan. 19, 2022

(65) Prior Publication Data
US 2022/0138980 A1    May 5, 2022
US 2023/0021299 A9    Jan. 19, 2023

Related U.S. Application Data

(63) Continuation of application No. 16/932,349, filed on Jul. 17, 2020, now Pat. No. 11,244,472, which is a (Continued)

(51) Int. Cl.
*G06T 7/00*    (2017.01)
*G06T 7/62*    (2017.01)
(Continued)

(52) U.S. Cl.
CPC ............ *G06T 7/12* (2017.01); *A61N 5/1049* (2013.01); *G06T 7/0012* (2013.01); *G06T 7/30* (2017.01);
(Continued)

(58) Field of Classification Search
CPC .... G06T 7/70; G06T 7/62; G06T 7/30; G06T 7/0012; G06T 2207/20128;
(Continued)

(56) References Cited

U.S. PATENT DOCUMENTS

| 10,610,203 | B2 | 4/2020 | Liang et al. |
| 2013/0077841 | A1 | 3/2013 | Wu et al. |
| 2014/0003695 | A1* | 1/2014 | Dean ............... A61B 5/7264 382/131 |

FOREIGN PATENT DOCUMENTS

| EP | 1563799 | 8/2005 |
| WO | 2004063988 | 7/2004 |
| WO | 2014023350 | 2/2014 |

OTHER PUBLICATIONS

International Bureau of WIPO, Transmittal of International Preliminary Report on Patentability issued for Application No. PCT/EP2019/063398. dated Nov. 16, 2021. 10 pages.
(Continued)

*Primary Examiner* — Siamak Harandi
(74) *Attorney, Agent, or Firm* — Gray Ice Higdon

(57) ABSTRACT

Disclosed is a computer-implemented method of determining one or more position and/or orientation parameters of an anatomical structure of a body portion. The anatomical structure has a longitudinal shape defining a longitudinal axis. The method includes generating and/or reading, by a data processing system, volumetric data of at least a portion of a subject. The method further includes generating and/or reading, by the data processing system, a deformable template which provides an estimate for a location of the longitudinal axis in the portion of the subject. The method further includes matching, by the data processing system, the deformable template to the volumetric data, thereby obtaining a matched template. The matching comprises using one or more internal energy functions and one or more external energy functions for optimizing an objective function. The method further includes determining, by the data processing system, the at least one position and/or orientation parameter based on the matched template.

20 Claims, 10 Drawing Sheets

(51) Int. Cl.
*G06T 7/12* (2017.01)
*G06T 7/30* (2017.01)
*G06T 7/70* (2017.01)
*A61N 5/10* (2006.01)
*G06V 10/44* (2022.01)
*G06V 10/75* (2022.01)

(52) U.S. Cl.
CPC ............... *G06T 7/62* (2017.01); *G06T 7/70* (2017.01); *G06V 10/443* (2022.01); *G06V 10/755* (2022.01); *G06T 2207/20128* (2013.01); *G06T 2207/30016* (2013.01); *G06T 2207/30101* (2013.01)

(58) Field of Classification Search
CPC . G06T 2207/30016; G06T 2207/30101; G06T 7/149; G06T 7/12; G06T 2207/20076; G06T 2207/10092; G06T 2200/04; A61N 5/1049; G06K 9/4609; G06K 9/6207; G06K 2209/051; G06V 10/443; G06V 10/753; G06V 10/755; G06V 2201/031
See application file for complete search history.

(56) References Cited

OTHER PUBLICATIONS

Tagare, "Deformable 2-D Template Matching Using Orthogonal Curves" IEEE Transactions on Medical Imaging, vol. 16, No. 1. Feb. 1997. 10 pages.

Sherbondy et al., "ConTrack: Finding the Most Likely Pathways Between Brain Regions Using Diffusion Tractography" Journal of Vision, 2008 8(9):15 1-16. Feb. 2008.

Cook et al., "Modelling Noise-Induced Fibre-Orientation Error in Diffusion-Tensor MRI" Dept. of Computer Science University Colleg London, Uk. IEEE 2004.

Eckstein et al., "Active Fibers: Matching Deformable Tract Templates to Diffusion Tensor Images" NeuroImage vol. 47 (2009) Elsevier Inc. Amsterdam, NL.

Tuch et al., "Q-Ball Imaging" Magnetic Resonance in Medicine 52:1358-1372 (2004).

International Search Report and Written Opinion for PCT/EP2019/063398 dated Jan. 30, 2020. 17 Pages.

Eckstein et al. "Active fibers: Matching deformable tract templates to diffusion tensor images", Neuroimage, Elsevier, Amsterdam, NL, vol. 47, Aug. 1, 2009, pp. T82-T89.

Mohan et al. "Tubular Surface Segmentation for Extracting Anatomical Structures From Medical Imagery", IEEE Transactions on Medical Imaging, IEEE Service Center, Piscataway, NJ, US, vol. 29, No. 12, Dec. 1, 2010, pp. 1945-1958.

Canadian Intellectual Property Office; Office Action issued in Application No. 3,088,626; 3 pages, dated Jun. 9, 2022.

European Patent Office; Communication Pursuant to Article 94(3) issued for Application No. 19726664.6, 6 pages, dated Feb. 28, 2022.

European Patent Office; Intention to Grant issued for Application No. 19726664.6, 7 pages, dated Oct. 17, 2022.

Jain et al., "Deformable template models: a review" Signal Processing, 71 (1998) 109-129. 1998.

\* cited by examiner

METHOD, SYSTEM AND COMPUTER PROGRAM FOR DETERMINING POSITION AND/OR ORIENTATION PARAMETERS OF AN ANATOMICAL STRUCTURE

FIELD OF THE INVENTION

The present invention relates to a computer-implemented method for determining at least one position and/or orientation parameter of an anatomical structure, a corresponding computer program, a non-transitory program storage medium storing such a program and a computer for executing the program, as well as a medical system comprising an electronic data storage device and the aforementioned computer.

TECHNICAL BACKGROUND

In neuroimaging, significant advances have been made during the last two decades which nowadays allow acquisition of high-resolution images using magnetic resonance imaging for highly detailed visualization of brain structures. These data can provide a valuable basis for pre-operative planning and intraoperative navigation.

In recent years, techniques for locating the brain white matter fibers using diffusion tensor magnetic resonance imaging (DTI-MRI) and fiber tracking (tractography) have made a tremendous progress.

Although these techniques can be used to reliably identify the major brain white matter fibers, it is still difficult to image small fiber bundles such as cranial nerves. The reason for this resides, inter alia, in the fact that the diameter of cranial nerves typically is much smaller than the data resolution obtained using diffusion tensor images.

Further, anatomical localization of brain white matter fiber bundles is a major challenge in cases where it is necessary to differentiate tumor from surrounding brain white matter. Specifically, adjacent tumors can make segmentation of fiber bundles more challenging and error-prone so that it is not possible to meet the required confidence level.

Most of current tractography techniques can be loosely grouped into two categories: deterministic and probabilistic. Deterministic tractography algorithms generate pathways from a seed region by making a sequence of discrete, locally optimal decisions. However, these algorithms do not account for uncertainty in the pathway: a pathway either exists or not so that valuable information about the reliability of the underlying data is lost. Further, deterministic algorithms do not consider pathways, which pass through small regions that violate deterministic rules and which may be caused by measurement artifacts, noise and unresolved features, such as crossing fiber tracts. This results in errors in the generated pathways.

While probabilistic tractography algorithms expand the pathway search space beyond that explored by deterministic algorithms and explicitly represent uncertainty in the data, probabilistic tractography algorithms also suffer from the limitation that they do not yield an accurate probability of brain connections. Therefore, like in deterministic tracking algorithms, prior knowledge of anatomy fiber tracts is important for distinguishing between fiber tracts of interest and tracks that follow improbable routes or suggest non-existent connections between brain areas. Moreover, probabilistic tractography algorithms typically require intensive computation which inhibits its application in routine clinical tasks.

A need for improvement also exists in analysis of volumetric image data which show other anatomical structures, such as ligaments, the spinal cord and vascular bodies.

Therefore, a need exists for method and systems, which allow a more accurate determination of position and/or orientation parameters of anatomical structures based on volumetric image data. This need is met by the subject-matter of the independent claims.

EXEMPLARY SHORT DESCRIPTION OF THE INVENTION

In the following, a short description of the specific features of the present invention is given which shall not be understood to limit the invention only to the features or a combination of the features described in this section.

Disclosed is a computer-implemented method of determining one or more position and/or orientation parameters, such as a shape, orientation and/or position of an anatomical structure of a body portion using a deformable template, which is matched to the volumetric data. The proposed method can be used for tracking bundles of brain white matter fibers, thereby representing a technique, which overcomes the limitations of conventional fiber tracking techniques, such as deterministic or probabilistic fiber tracking algorithms. The proposed method can also be used for efficiently determining the extent of other anatomical structures, such as ligaments, the spinal cord, tubular anatomical structures, such as vascular bodies (e.g. blood vessels) and bundles of brain white matter fibers (such as cranial nerves).

GENERAL DESCRIPTION OF THE INVENTION

In this section, a description of the general features of the present invention is given for example by referring to possible embodiments of the invention.

In a first aspect, the invention is directed to a computer-implemented method of determining one or more position and/or orientation parameters of an anatomical structure of a body portion. The anatomical structure has a longitudinal shape which defined a longitudinal axis. The method comprises generating and/or reading, by a data processing system, volumetric data of at least a portion of a subject. The method further comprises generating, by the data processing system, a deformable template which provides an estimate for a location of the longitudinal axis in the portion of the subject. The method further comprises matching, by the data processing system, the deformable template to the volumetric data, thereby obtaining a matched template. The matching comprises using one or more internal energy functions and one or more external energy functions for optimizing an objective function. The method further comprises determining, by the data processing system, the at least one position and/or orientation parameter based on the matched template.

The volumetric data are three-dimensional data having a plurality of voxels. The volumetric data may be generated using an image acquisition system, which is in signal communication with the data processing system. By way of example, the volumetric data may be generated using diffusion tensor magnetic resonance imaging. The volumetric data may include, for each of the plurality of voxels of the volumetric data, values of a diffusion tensor.

The determined position and/or orientation parameters may be indicative of a shape, location and/or orientation of the longitudinal axis in three-dimensional space. At least a portion of the longitudinal axis may have a curved shape.

The longitudinal axis may be a central longitudinal axis and/or an axis of symmetry of the anatomical structure.

The anatomical structure may represent an anatomically and/or functionally defined portion of the body. Examples for the anatomical structure are but are not limited to: ligaments, the spinal cord, tubular anatomical structures, such as vascular bodies (e.g. blood vessels) and bundles of brain white matter fibers (such as cranial nerves). Examples for for cranial nerves are but are not limited to Trigeminal Nerve, Facial Nerve and Vestibulocochlear Nerve. A diameter of the brain white matter fiber bundle may be smaller than 10 millimeter or smaller than 5 millimeter. The diameter may be greater than 0.3 millimeter or greater than 0.5 millimeter.

The objective function may be a function (in particular a sum or a weighted sum) of the one or more internal energy functions and the one or more external energy functions. Optimization of the objective function may include minimizing or maximizing the objective function. The one or more internal and/or the one or more external energy functions may depend on the positions of the position adjustable control points.

The term "internal energy function" may be defined to mean an energy function which depends on one or more intrinsic geometrical parameters of the curves of the deformable template and and/or on a prototype of the template. The internal energy function may be independent from the volumetric data. For each of the curves, an internal energy may be defined depending on the one or more energy functions. The internal energy may penalize a low degree of smoothness of the curve and/or a large distance from the prototype.

The term "external energy function" may be defined to mean an energy function which depends on the volumetric image data. For each of the curves, an external energy may be defined depending on the one or more external energy functions. The external energy may be configured to penalize a low degree of data fidelity of the curve. The external energy may be determined using voxel data values of the volumetric data at one or more locations of the curve.

The deformable template may represent a plurality of curves, each of which representing an approximation for the longitudinal axis. The shape, location and/or orientation of the curves may depend on a plurality of parameters. Each of the parameters may be variable over a predefined range. Each of the curves may be at least partially defined using a plurality of position adjustable control points. Each of the control points may be located on the curve. In an alternative embodiment, at least a portion of the control points is located at a distance from the curve.

In an example of the method, the deformable template comprises, for each of the control points, a discrete search space having a plurality of search space points for positioning the control points.

In an example of the method, for one or more of the control points, the search space points for the respective control point form a plane or curved surface.

In an example of the method, for one or more of the curves, at least a portion of the curve is a spline curve, such as a Bezier curve and/or a NURBS (non-uniform rational B-spline) curve. A degree of the spline curve may be 1 or greater than 1. A spline curve of degree 1 is a polygonal chain.

In an example of the method, for at least a portion of the control points, the search spaces of the control points are mutually non-overlapping.

In an example of the method, for one or more of the control points, the search space points for the respective control point form a plane or curved surface.

In a further example of the method, each of the curves is a polygonal chain having a plurality of line segments. Each of the segments may connect two of the position adjustable control points. The line segments of the polygonal chain may be straight line segments.

In an example of the method, at least one of the one or more internal energy functions is a function of an angle formed between a line segment of the polygonal chain and one of the surfaces.

In an example of the method, at least one of the one or more internal energy functions is a function of an angle formed between two neighboring line segments of the polygonal chain.

In an example of the method, the objective (OF) comprises or consists of a sum of subfunctions, which depends on all control points. Each of the subfunctions may depend on positions of directly consecutive control points, as seen along the curve. Additionally or alternatively, each of the subfunctions may be independent from the remaining control points.

In an example of the method, the method includes determining, for each search space point of a first one of the control points, an optimized energy value based on sections of the curves, which end at the respective search space point. The optimized energy value may be determined using one or a sum of the subfunctions. For each of the curve sections, the one or the sum of the subfunctions may correspond to the respective curve section. For each of the sections, an opposite end of the respective section may start at a same search space point of a same control point.

In an example of the method, the method includes determining, for each search space point of a second one of the control points, an optimized energy value based on sections of the curves. Each of the sections may end at the respective search space point. Each of the sections may pass through the search space of the first control point. The second control point may be a directly consecutive control point to the first control point, when seen along the curve. The optimized energy value may be determined based on the optimized energy values determined for the first control point. Additionally or alternatively, the optimized energy value may be determined based on the subfunction which depends on the first and second control point. Each of the sections may pass through a different search space point of the first control point. For each search space point of the second control point, the optimized energy value may be determined by optimizing a sum of the optimized energy value, which corresponds to a search space point of the first control point and the subfunction. The optimization may include varying the search space point of the first control point. For each of the sections, an opposite end of the respective section may start at a same search space point of a same control point.

In an example of the method, each of the subfunctions further depends on two radius values, each of which representing a radius of the anatomical structure at one of the consecutive control points.

In an example of the method, at least one of the external energy functions is a function of locations of the control points and further a function of radius values of the anatomical structure at the locations of the control points.

In an example of the method, the method further includes generating, by the data processing system, segmentation data depending on the volumetric data. The segmentation data may indicate, for each of a plurality of voxels of the volumetric data, an estimate, whether the respective voxel represents a part of the anatomical structure. The segmentation data may be determined using an atlas-based segmentation method. The prototype of the deformable template may be generated using the segmentation data.

In an example of the method, the volumetric data includes, for each of one or more voxels, directional diffusion data. By way of example, for each of the voxels, the directional diffusion data include one or more values of a diffusion tensor. The directional diffusion data of the voxels may include diffusion-weighted magnetic resonance data. The diffusion-weighted magnetic resonance data may include a plurality of diffusion-weighted volumetric images, in particular 6 or more diffusion-weighted volumetric images. The diffusion-weighted volumetric images may be acquired at different points in q-space. The q-space may be defined as the diffusion frequency space, measured in units of inverse length. Additionally, the diffusion-weighted magnetic resonance data may include a baseline b0 volumetric image.

For each of the voxels, the directional diffusion data may be indicative of a directional anisotropy of an apparent diffusion coefficient at the respective voxel. The diffusion may be a diffusion of water. The directional diffusion data may be generated using one or more techniques of diffusion weighted imaging. By way of example, the directional diffusion data may be generated using diffusion tensor imaging (DTI), diffusion spectrum imaging (DSI), high angular resolution diffusion imaging (HARDI), (in particular Q-ball imaging (QBI)), and hybrid diffusion imaging (HYDI). The q-space is the diffusion frequency space, measured in $\mu m^{-1}$.

For performing q-space imaging, a 3D grid representing a volume in the q-space may be sampled. This technique is commonly referred to as diffusion spectrum imaging (DSI). Alternatively, one or more shells in q-space may be sampled. Each shell may represent q-values of substantially a same b-value. These techniques are commonly referred to as single-shell angular resolution diffusion imaging (HARDI) or multi-shell HARDI. Alternatively, hybrid sampling schemes may be used, such as radial sampling along radial lines, which extend from the origin of the q-space. These techniques are commonly referred to as hybrid diffusion imaging (HYDI).

In an example of the method, the method further includes determining, for each of a plurality of voxels of the volumetric data, one or more values of an orientation probability density function of an orientation of the longitudinal axis of the anatomical structure. The values of the orientation probability density function may be determined based on one or more values of the volumetric data of the respective voxel, in particular based on one or more values of directional diffusion data of the respective voxel, in particular based on one or more values of the diffusion tensor of the respective voxel. The orientation probability density function, may indicate, for each of a plurality of directions at the respective voxel, a probability value that the longitudinal axis of the anatomical structure is oriented along the respective direction. At least one of the one or more external energy functions may be determined based on the determined values of the orientation probability density function. Determining the external energy function for a curve of the deformable template may include evaluating, for each of a number of points on the curve and/or for each of a plurality of the control points of the curve, the orientation probability density function at the respective point. The orientation probability density function may be evaluated for a direction, which corresponds to a tangent of the curve at the respective point.

In an example of the method, at least one of the internal energy functions depends on a distance of one or more control points of the deformable template from a prototype of the deformable template. The distance may be the shortest distance measured between a control point of a curve of the template and the corresponding control point of the prototype.

In an example of the method, the anatomical structure is at least a portion of a nerve fiber or at least a portion of a bundle of nerve fibers. In an example of the method, the anatomical structure is at least a portion of a ligament, a spinal cord, or a tubular anatomical structure.

In a second aspect, the invention is directed to a computer program which, when running on at least one processor (for example, a processor) of at least one computer (for example, a computer) or when loaded into at least one memory (for example, a memory) of at least one computer (for example, a computer), causes the at least one computer to perform the above-described method according to the first aspect. The invention may alternatively or additionally relate to a (physical, for example electrical, for example technically generated) signal wave, for example a digital signal wave, carrying information which represents the program, for example the aforementioned program, which for example comprises code means which are adapted to perform any or all of the steps of the method according to the first aspect. A computer program stored on a disc is a data file, and when the file is read out and transmitted it becomes a data stream for example in the form of a (physical, for example electrical, for example technically generated) signal. The signal can be implemented as the signal wave which is described herein. For example, the signal, for example the signal wave is constituted to be transmitted via a computer network, for example LAN, WLAN, WAN, for example the internet. The invention according to the second aspect therefore may alternatively or additionally relate to a data stream representative of the aforementioned program.

In a third aspect, the invention is directed to a non-transitory computer-readable program storage medium on which the program according to the second aspect is stored.

In a fourth aspect, the invention is directed to at least one computer (for example, a computer), comprising at least one processor (for example, a processor) and at least one memory (for example, a memory), wherein the program according to the fourth aspect is running on the processor or is loaded into the memory, or wherein the at least one computer comprises the computer-readable program storage medium according to the third aspect.

In a fifth aspect, the invention is directed to a medical system, comprising the at least one computer according to the fourth aspect; at least one electronic data storage device storing at least the determined one or more position and/or orientation data; and a medical device for carrying out a medical procedure on the patient, wherein the at least one computer is operably coupled to the at least one electronic data storage device for acquiring, from the at least one data storage device, at least the patient data, and the medical device for issuing a control signal to the medical device for controlling the operation of the medical device on the basis of the result of applying the filter rule to the medical information and, as far as the program causes the at least one computer to determine the selection data, the selected medical image information.

In an example of the system according to the fifth aspect, the medical device comprises a radiation treatment apparatus comprising a treatment beam source and a patient support unit (such as at least one of a patient bed or a headrest). The at least one computer is then operably coupled to the radiation treatment apparatus for issuing a control signal to the radiation treatment apparatus for controlling operation of the radiation treatment apparatus, on the basis of the determined one or more position and/or orientation parameters. The treatment beam source may be configured to generate a treatment beam. The treatment beam may include photon rays and/or a particle rays. The photon rays may include X-rays and/or gamma rays. The particle rays may include charged particles, such as protons and/or ions (such as carbon (C), boron (B) and/or neon (Ne) ions). Additionally or alternatively, the particle rays may include non-charged particles, such as neutrons.

In an example of the system, the medical device comprises: a radiotherapy and/or radiosurgery system for conducting a medical procedure, wherein the at least one computer is operably coupled to the radiotherapy and/or radiosurgery system for issuing a control signal to the radiotherapy and/or radiosurgery system for controlling, on the basis of the determined at least one position and/or orientation parameter of the anatomical structure, the operation of the radiotherapy and/or radiosurgery system. The radiotherapy and/or radiosurgery system may include a beam source for generating a beam. The beam may include photon rays and/or a particle rays. The photon rays may include X-rays and/or gamma rays. The particle rays may include charged particles, such as protons and/or ions (such as carbon (C), boron (B) and/or neon (Ne) ions). Additionally or alternatively, the particle rays may include non-charged particles, such as neutrons.

In an example of the system according to the fifth aspect, the medical system comprises a data processing system and/or a data acquisition system. The data acquisition system may be configured to acquire the volumetric data. The data acquisition system may include one or more of: a computed tomography (CT) system, a cone beam computed tomography (CBCT, such as volumetric CBCT) system, an x-ray tomography, magnetic resonance tomography (MRT or MRI) system, a sonography system, an ultrasound examinations, and a positron emission tomography system.

The magnetic resonance imaging system may be configured to perform diffusion-weighted magnetic resonance imaging In particular, the magnetic resonance imaging system may be configured to perform one or a combination of: diffusion tensor magnetic resonance imaging, high angular resolution diffusion imaging (HARDI), Q-ball imaging and diffusion spectrum imaging (DSI). The diffusion-weighted magnetic resonance imaging may be configured to measure, for each of a plurality of voxels, one or more values of a diffusion tensor.

The data processing system may be implemented by a computer having a processor and a memory for storing instructions processable by the processor. The processor may execute an operating system. The data processing system may further include an input and/or output unit configured to allow a user to receive data from the data processing system and/or to provide data to the data processing system. The computer system may further include a data storage system and/or a user interface for receiving user input.

Computer Implemented Method

The method in accordance with the invention is for example a computer implemented method. For example, all the steps or merely some of the steps (i.e. less than the total number of steps) of the method in accordance with the invention can be executed by a computer (for example, at least one computer). An embodiment of the computer implemented method is a use of the computer for performing a data processing method. An embodiment of the computer implemented method is a method concerning the operation of the computer such that the computer is operated to perform one, more or all steps of the method.

The computer for example comprises at least one processor and for example at least one memory in order to (technically) process the data, for example electronically and/or optically. The processor being for example made of a substance or composition which is a semiconductor, for example at least partly n- and/or p-doped semiconductor, for example at least one of II-, III-, IV-, V-, VI-semiconductor material, for example (doped) silicon and/or gallium arsenide. The calculating or determining steps described are for example performed by a computer. Determining steps or calculating steps are for example steps of determining data within the framework of the technical method, for example within the framework of a program. A computer is for example any kind of data processing device, for example electronic data processing device. A computer can be a device which is generally thought of as such, for example desktop PCs, notebooks, netbooks, etc., but can also be any programmable apparatus, such as for example a mobile phone or an embedded processor. A computer can for example comprise a system (network) of "sub-computers", wherein each sub-computer represents a computer in its own right. The term "computer" includes a cloud computer, for example a cloud server. The term "cloud computer" includes a cloud computer system which for example comprises a system of at least one cloud computer and for example a plurality of operatively interconnected cloud computers such as a server farm. Such a cloud computer is preferably connected to a wide area network such as the world wide web (WWW) and located in a so-called cloud of computers which are all connected to the world wide web. Such an infrastructure is used for "cloud computing", which describes computation, software, data access and storage services which do not require the end user to know the physical location and/or configuration of the computer delivering a specific service. For example, the term "cloud" is used in this respect as a metaphor for the Internet (world wide web). For example, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer for example comprises interfaces in order to receive or output data and/or perform an analogue-to-digital conversion. The data are for example data which represent physical properties and/or which are generated from technical signals. The technical signals are for example generated by means of (technical) detection devices (such as for example devices for detecting marker devices) and/or (technical) analytical devices (such as for example devices for performing (medical) imaging methods), wherein the technical signals are for example electrical or optical signals. The technical signals for example represent the data received or outputted by the computer. The computer is preferably operatively coupled to a display device which allows information outputted by the computer to be displayed, for example to a user. One example of a display device is a virtual reality device or an augmented reality device (also referred to as virtual reality glasses or augmented reality glasses) which can be used as "goggles" for navigating. A specific example of such augmented reality glasses is Google Glass (a trademark of Google, Inc.). An augmented reality device or a virtual reality device can be used both to input information into the computer by user interaction and to display information outputted by the computer. Another example of a display device would be a standard computer monitor comprising for example a liquid crystal display operatively coupled to the computer for receiving display control data from the computer for generating signals used to display image information content on the display device. A specific embodiment of such a computer monitor is a digital lightbox. An example of such a digital lightbox is Buzz®, a product of Brainlab AG. The monitor may also be the monitor of a portable, for example handheld, device such as a smart phone or personal digital assistant or digital media player.

The invention also relates to a program which, when running on a computer, causes the computer to perform one or more or all of the method steps described herein and/or to a program storage medium on which the program is stored (in particular in a non-transitory form) and/or to a computer comprising said program storage medium and/or to a (physical, for example electrical, for example technically generated) signal wave, for example a digital signal wave, carrying information which represents the program, for example the aforementioned program, which for example comprises code means which are adapted to perform any or all of the method steps described herein.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, for example computer-readable data storage medium comprising computer-usable, for example computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, for example a data processing device comprising a digital processor (central processing unit or CPU) which executes the computer program elements, and optionally a volatile memory (for example a random access memory or RAM) for storing data used for and/or produced by executing the computer program elements. Within the framework of the present invention, a computer-usable, for example computer-readable data storage medium can be any data storage medium which can include, store, communicate, propagate or transport the program for use on or in connection with the instruction-executing system, apparatus or device. The computer-usable, for example computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the invention in the example embodiments. The computer and/or data processing device can for example include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or a vibration element incorporated into an instrument). For the purpose of this document, a computer is a technical computer which for example comprises technical, for example tangible components, for example mechanical and/or electronic components. Any device mentioned as such in this document is a technical and for example tangible device.

Acquiring Data

The expression "acquiring data" for example encompasses (within the framework of a computer implemented method) the scenario in which the data are determined by the computer implemented method or program. Determining data for example encompasses measuring physical quantities and transforming the measured values into data, for example digital data, and/or computing (and e.g. outputting) the data by means of a computer and for example within the framework of the method in accordance with the invention. The meaning of "acquiring data" also for example encompasses the scenario in which the data are received or retrieved by (e.g. input to) the computer implemented method or program, for example from another program, a previous method step or a data storage medium, for example for further processing by the computer implemented method or program. Generation of the data to be acquired may but need not be part of the method in accordance with the invention. The expression "acquiring data" can therefore also for example mean waiting to receive data and/or receiving the data. The received data can for example be inputted via an interface. The expression "acquiring data" can also mean that the computer implemented method or program performs steps in order to (actively) receive or retrieve the data from a data source, for instance a data storage medium (such as for example a ROM, RAM, database, hard drive, etc.), or via the interface (for instance, from another computer or a network). The data acquired by the disclosed method or device, respectively, may be acquired from a database located in a data storage device which is operably to a computer for data transfer between the database and the computer, for example from the database to the computer. The computer acquires the data for use as an input for steps of determining data. The determined data can be output again to the same or another database to be stored for later use. The database or database used for implementing the disclosed method can be located on network data storage device or a network server (for example, a cloud data storage device or a cloud server) or a local data storage device (such as a mass storage device operably connected to at least one computer executing the disclosed method). The data can be made "ready for use" by performing an additional step before the acquiring step. In accordance with this additional step, the data are generated in order to be acquired. The data are for example detected or captured (for example by an analytical device). Alternatively or additionally, the data are inputted in accordance with the additional step, for instance via interfaces. The data generated can for example be inputted (for instance into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. The step of "acquiring data" can therefore also involve commanding a device to obtain and/or provide the data to be acquired. In particular, the acquiring step does not involve an invasive step which would represent a substantial physical interference with the body, requiring professional medical expertise to be carried out and entailing a substantial health risk even when carried out with the required professional care and expertise. In particular, the step of acquiring data, for example determining data, does not involve a surgical step and in particular does not involve a step of treating a human or animal body using surgery or therapy. In order to distinguish the different data used by the present method, the data are denoted (i.e. referred to) as "XY data" and the like and are defined in terms of the information which they describe, which is then preferably referred to as "XY information" and the like.

Navigation System

The present invention is also directed to a navigation system for computer-assisted surgery. This navigation system preferably comprises the aforementioned computer for processing the data provided in accordance with the computer implemented method as described in any one of the embodiments described herein. The navigation system preferably comprises a detection device for detecting the position of detection points which represent the main points and auxiliary points, in order to generate detection signals and to supply the generated detection signals to the computer, such that the computer can determine the absolute main point data and absolute auxiliary point data on the basis of the detection signals received. A detection point is for example a point on the surface of the anatomical structure which is detected, for example by a pointer. In this way, the absolute point data can be provided to the computer. The navigation system also preferably comprises a user interface for receiving the calculation results from the computer (for example, the position of the main plane, the position of the auxiliary plane and/or the position of the standard plane). The user interface provides the received data to the user as information. Examples of a user interface include a display device such as a monitor, or a loudspeaker. The user interface can use any kind of indication signal (for example a visual signal, an audio signal and/or a vibration signal). One example of a display device is an augmented reality device (also referred to as augmented reality glasses) which can be used as so-called "goggles" for navigating. A specific example of such augmented reality glasses is Google Glass (a trademark of Google, Inc.). An augmented reality device can be used both to input information into the computer of the navigation system by user interaction and to display information outputted by the computer.

The invention also relates to a navigation system for computer-assisted surgery, comprising: a computer for processing the absolute point data and the relative point data; a detection device for detecting the position of the main and auxiliary points in order to generate the absolute point data and to supply the absolute point data to the computer; a data interface for receiving the relative point data and for supplying the relative point data to the computer; and a user interface for receiving data from the computer in order to provide information to the user, wherein the received data are generated by the computer on the basis of the results of the processing performed by the computer.

Surgical Navigation System

A navigation system, such as a surgical navigation system, is understood to mean a system which can comprise: at least one marker device; a transmitter which emits electromagnetic waves and/or radiation and/or ultrasound waves; a receiver which receives electromagnetic waves and/or radiation and/or ultrasound waves; and an electronic data processing device which is connected to the receiver and/or the transmitter, wherein the data processing device (for example, a computer) for example comprises a processor (CPU) and a working memory and advantageously an indicating device for issuing an indication signal (for example, a visual indicating device such as a monitor and/or an audio indicating device such as a loudspeaker and/or a tactile indicating device such as a vibrator) and a permanent data memory, wherein the data processing device processes navigation data forwarded to it by the receiver and can advantageously output guidance information to a user via the indicating device. The navigation data can be stored in the permanent data memory and for example compared with data stored in said memory beforehand.

Atlas/Atlas Segmentation

Preferably, atlas data is acquired which describes (for example defines, more particularly represents and/or is) a general three-dimensional shape of the anatomical body part, such as the anatomical structure. The atlas data therefore represents an atlas of the anatomical body part, such as the anatomical structure. An atlas may consist of one or more generic models of objects. The generic models of the objects together may form a complex structure. For example, the atlas may constitute a statistical model of a patient's body (for example, a part of the body) which has been generated from anatomic information gathered from a plurality of human bodies, for example from medical image data containing images of such human bodies. In principle, the atlas data therefore may represent the result of a statistical analysis of such medical image data for a plurality of human bodies. This result can be output as an image—the atlas data therefore contains or is comparable to medical image data. Such a comparison can be carried out for example by applying an image registration algorithm which conducts registration between the atlas data and the medical image data. The result of the comparison can be a measure of similarity between the atlas data and the medical image data. The atlas data comprises image information (for example, positional image information) which can be matched or registered (for example by applying an elastic or rigid image fusion algorithm) for example to image information (for example, positional image information) contained in medical image data, such as the volumetric data acquired using the data acquisition system, so as to for example compare the atlas data to the medical image data in order to determine the position of anatomical structures in the medical image data which correspond to anatomical structures defined by the atlas data.

The human bodies, the anatomy of which serves as an input for generating the atlas data, advantageously share a common feature such as at least one of gender, age, ethnicity, body measurements (e.g. size and/or mass) and pathologic state. The anatomic information describes for example the anatomy of the human bodies and is extracted for example from medical image information about the human bodies. The atlas of a femur, for example, can comprise the head, the neck, the body, the greater trochanter, the lesser trochanter and the lower extremity as objects which together make up the complete structure. The atlas of a brain, for example, can comprise the telencephalon, the cerebellum, the diencephalon, the pons, the mesencephalon and the medulla as the objects which together make up the complex structure. One application of such an atlas is in the segmentation of medical images, in which the atlas is matched to medical image data, and the image data are compared with the matched atlas in order to assign a point (a pixel or voxel) of the image data to an object of the matched atlas, thereby segmenting the image data into objects.

Imaging Methods

In the field of medicine, imaging methods (also called imaging modalities and/or medical imaging modalities) are used to generate image data (for example, two-dimensional or three-dimensional image data), such as the volumetric data, of anatomical structures (such as soft tissues, bones, organs, etc.) of the human body. The term "medical imaging methods" is understood to mean (advantageously apparatus-based) imaging methods (for example so-called medical imaging modalities and/or radiological imaging methods) such as for instance computed tomography (CT) and cone beam computed tomography (CBCT, such as volumetric CBCT), x-ray tomography, magnetic resonance tomography (MRT or MRI), conventional x-ray, sonography and/or ultrasound examinations, and positron emission tomography. For example, the medical imaging methods are performed by the analytical devices, such as the data acquisition system, which acquires the volumetric image data. Examples for medical imaging modalities applied by medical imaging methods are: X-ray radiography, or ultrasound, endoscopy, elastography, tactile imaging, thermography, medical photography and nuclear medicine functional imaging techniques as positron emission tomography (PET) and Single-photon emission computed tomography (SPECT), as mentioned by Wikipedia.

The image data, such as the volumetric data, thus generated is also termed "medical imaging data". Analytical devices for example are used to generate the image data in apparatus-based imaging methods. The imaging methods are for example used for medical diagnostics, to analyze the anatomical body in order to generate images which are described by the image data. The imaging methods are also for example used to detect pathological changes in the human body. However, some of the changes in the anatomical structure, such as the pathological changes in the structures (tissue), may not be detectable and for example may not be visible in the images generated by the imaging methods. A tumour represents an example of a change in an anatomical structure. If the tumour grows, it may then be said to represent an expanded anatomical structure. This expanded anatomical structure may not be detectable; for example, only a part of the expanded anatomical structure may be detectable. Primary/high-grade brain tumours are for example usually visible on MRI scans when contrast agents are used to infiltrate the tumour. MRI scans represent an example of an imaging method. In the case of MRI scans of such brain tumours, the signal enhancement in the MRI images (due to the contrast agents infiltrating the tumour) is considered to represent the solid tumour mass. Thus, the tumour is detectable and for example discernible in the image generated by the imaging method. In addition to these tumours, referred to as "enhancing" tumours, it is thought that approximately 10% of brain tumours are not discernible on a scan and are for example not visible to a user looking at the images generated by the imaging method.

BRIEF DESCRIPTION OF THE DRAWINGS

In the following, the present disclosure is described with reference to the appended Figures which give background explanations and represent exemplary embodiments of the invention. The scope of the invention is however not limited to the specific features disclosed in the context of the Figures, wherein.

DETAILED DESCRIPTION OF EXEMPLARY EMBODIMENTS

In the following, a short description of the specific features of the present disclosure is given which shall not be understood to limit the invention only to the features or a combination of the features described in this section.

Figure 1:
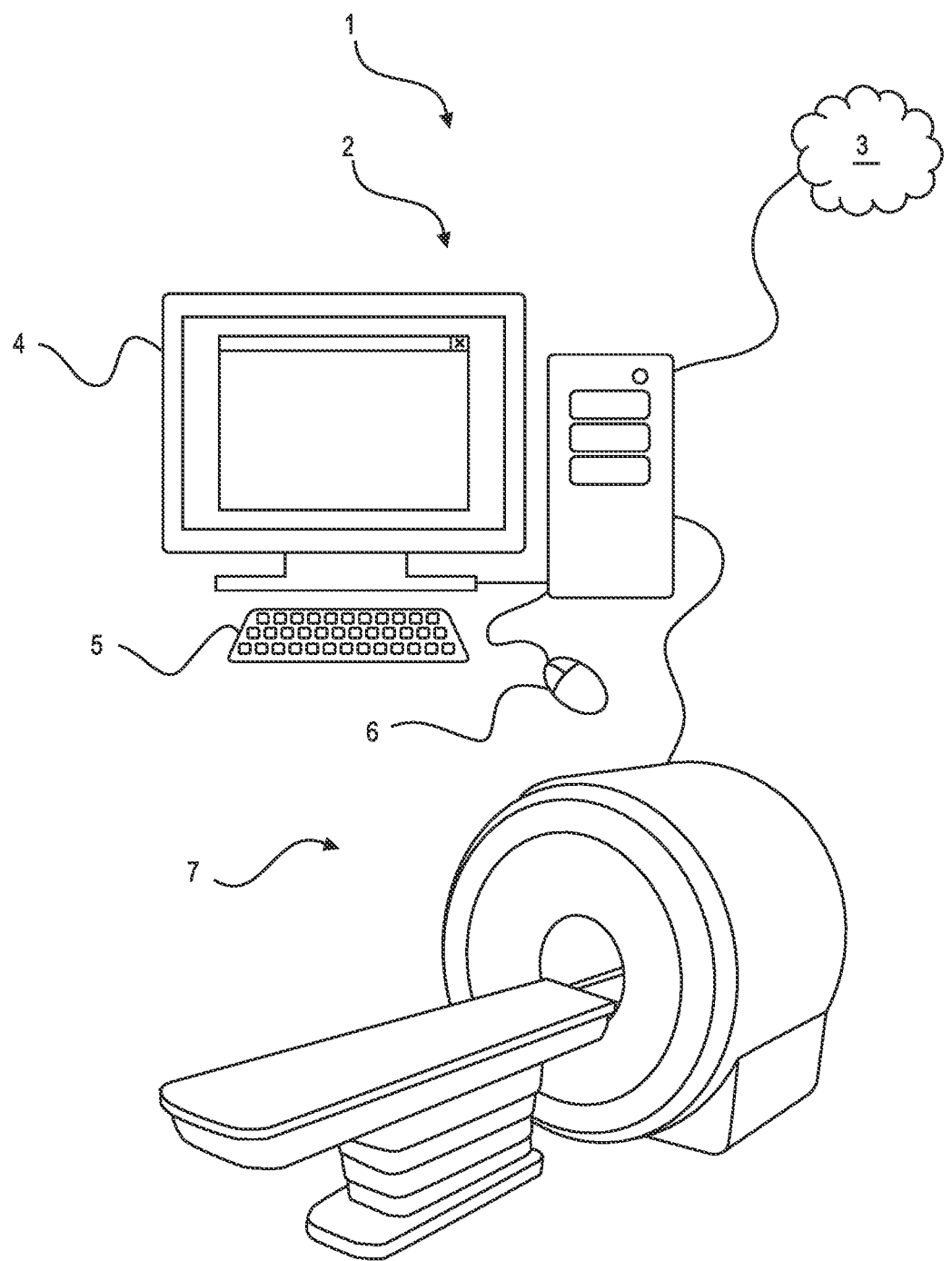
FIG. 1 is a schematic illustration of a medical system according to an exemplary embodiment.

FIG. 1 is a schematic illustration of a medical system 1 according to an exemplary embodiment. The medical system 1 includes a data processing system 2 and a data acquisition system 7, which is in signal communication with the data processing system 2. In the exemplary embodiment shown in FIG. 1, the data acquisition system 7 is configured as a magnetic resonance tomography system. It is to be understood, however, that the present disclosure is not limited to data acquisition systems, which include magnetic resonance tomography systems, but encompasses all embodiments of data acquisition systems, which are configured to acquired volumetric data from a subject under inspection.

The data processing system 2 may be a stand-alone computer or may be configured as a distributed computer system which uses a computer network 3, such as the Internet or a local area network (LAN). The data processing system 2 includes a display device 4 and input devices, such as a keyboard 5 and a computer mouse 6 allowing user interaction via a graphical user interface of the data processing system 2.

Figure 2:
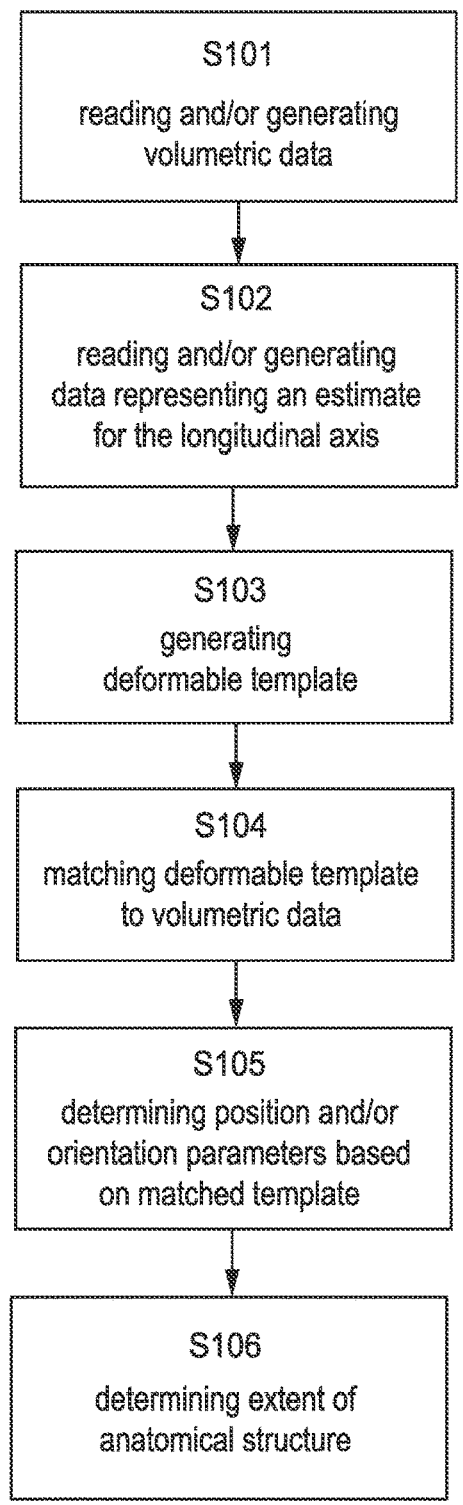
FIG. 2 is a flow chart illustrating an exemplary method for determining one or more position and/or orientation parameters of an anatomical structure of a body portion performed by the medical system according to the exemplary embodiment shown in FIG. 1.

FIG. 2 is a flow chart illustrating an exemplary method 100 performed using the medical system 1 which is schematically illustrated in FIG. 1.

The data processing system 2 is configured to read and/or generate S101 volumetric data of at least a portion of the subject. By way of example, the data processing system 2 may read the volumetric data from the data acquisition system 7 and/or may be configured to generate the volumetric data from data from the data acquisition system 7 and/or from signals received from the data acquisition system 7.

In the exemplary embodiment, which is shown in FIG. 1, the data acquisition system 7 is configured to perform diffusion tensor magnetic resonance imaging, which is a technique of diffusion-weighted magnetic resonance imaging and which has been shown to be able to depict brain white matter bundles.

In order to perform diffusion tensor magnetic resonance imaging, the data processing system 2 or the data acquisition system 7 (such as a further data processing system which is part of the data acquisition system 7) is configured to generate, depending on data acquired from a subject under inspection, for each of a plurality of voxels, values of a diffusion tensor. The diffusion tensor D is a [3×3] symmetric matrix:

$$D = \begin{bmatrix} D_{xx} & D_{xy} & D_{xz} \\ D_{yx} & D_{yy} & D_{yz} \\ D_{zx} & D_{zy} & D_{zz} \end{bmatrix},$$

where each of the three diagonal elements ($D_{xx}$, $D_{yy}$, $D_{zz}$) represents an apparent diffusion coefficient measured along one of the laboratory axes (i.e. the x-, y- and the z-axis). Each of the six off-diagonal terms ($D_{xy}$, $D_{yz}$, etc.) reflect the correlation of random motion between a pair of directions, which correspond to two different laboratory axes.

For the special case of perfect isotropic diffusion (such as seen in pure liquids), the off-diagonal elements are all zero and the diagonal elements are all the same and equal the single diffusion coefficient, $D_0$, for the isotropic material (i.e. $D_{xx}=D_{yy}=D_{zz}=D_0$). For anisotropic diffusion, however, as it occurs in diffusion tensor magnetic resonance imaging of brain white matter, for at least a portion of the voxels, the diagonal elements of the diffusion tensor are unequal and the off-diagonal elements cannot be ignored.

Figure 3A:
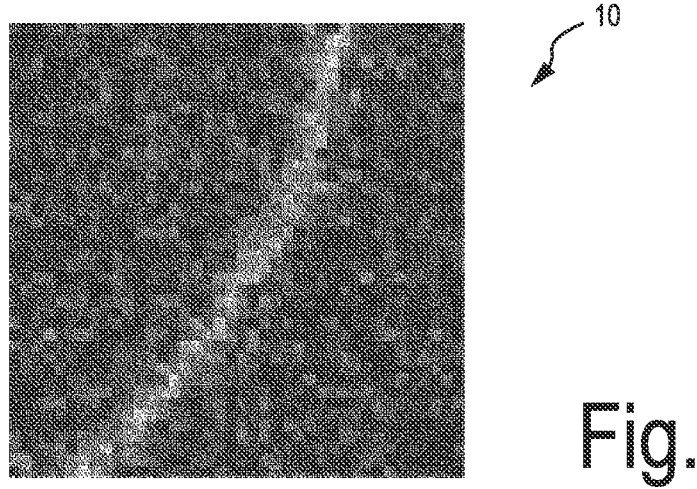
FIG. 3A is a cross-section through volumetric data which are acquired and analyzed using the medical system according to the exemplary embodiment, which is shown in FIG. 1.

FIG. 3A schematically illustrates a two-dimensional cross-section 10 through a volumetric data set generated using the medical system 1 (shown in FIG. 1). In FIG. 3A, for each of the voxels, the grayscale value of the two-dimensional cross-section 10 indicates a level of fractional anisotropy (commonly abbreviated as FA) at the respective voxel, which is determined using values of the diffusion tensor at the respective voxel.

The FA level is a scalar value between 0 and 1 that describes the degree of anisotropy of a diffusion process. A value of 1 (which represents a theoretical extreme) means that diffusion occurs only along one axis and is fully restricted along all other directions. The FA level is calculated from the eigenvalues $\lambda_1$, $\lambda_2$ and $\lambda_3$ of the diffusion tensor using the equation:

$$FA = \sqrt{\frac{3}{2}} \frac{\sqrt{(\lambda_1 - \hat{\lambda})^2 + (\lambda_2 - \hat{\lambda})^2 + (\lambda_3 - \hat{\lambda})^2}}{\sqrt{\lambda_1^2 + \lambda_2^2 + \lambda_3^2}},$$

with $\hat{\lambda}=(\lambda_1+\lambda_2+\lambda_3)/3$ being the mean value of the eigenvalues.

Therefore, a high FA level means a more unidirectional flow whereas a low FA level means equal water movement in all directions. As such, as a general rule, image regions of brighter grayscale values indicate greater white matter anisotropy which may be caused by highly organized fiber bundles which are present at the image region.

It is to be noted that in the exemplary method, the FA values are used for illustrating the performance of the invention so that is not necessary to determine values of the FA for performing the exemplary method. On the other hand, it is also conceivable that one or more of the external energy functions of the deformable template are determined using values of FA.

It is known in the prior art to use deterministic or probabilistic fiber tracking algorithms to determine the extent of brain white matter fiber bundles based on diffusion tensor imaging data. These methods, however, have shown to suffer from significant limitations.

Specifically, deterministic fiber tacking methods do not account for uncertainty in the determined pathway so that valuable information about the underlying diffusion tensor imaging data is lost. Further, deterministic fiber tracking methods do not consider pathways, which pass through small regions that violate deterministic rules and which may be caused by measurement artefacts, noise and unresolved features, such as crossing fiber tracts.

While probabilistic tractography algorithms expand the pathway search space beyond that explored by deterministic algorithms and explicitly represent uncertainty in the data, probabilistic tractography algorithms also suffer from the limitation that they do not yield an accurate probability of brain connections. Therefore, like deterministic tracking algorithms, prior knowledge of anatomy fiber tracts is important for distinguishing between fiber tracts of interest and tracks that follow improbable routes or suggest non-existent connections between brain areas. Moreover, probabilistic tractography algorithms typically require intensive computation which inhibits its application in routine clinical tasks.

However, as is explained in the following, in view of the above-described limitations of conventional fiber tracking algorithms, the present inventors have recognized that it is possible to provide an improved method for fiber tracking. As is also explained further below, the inventors also have recognized that it is possible to provide an improved analysis procedure for other anatomical structures than brain white matter fiber bundles, such as vascular anatomical structures, and particularly blood vessels.

As is indicated in the flow chart of FIG. 2, the data processing system is configured to read and/or to generate S102 data representing an estimate for a longitudinal axis of the anatomical structure.

Figure 3B:
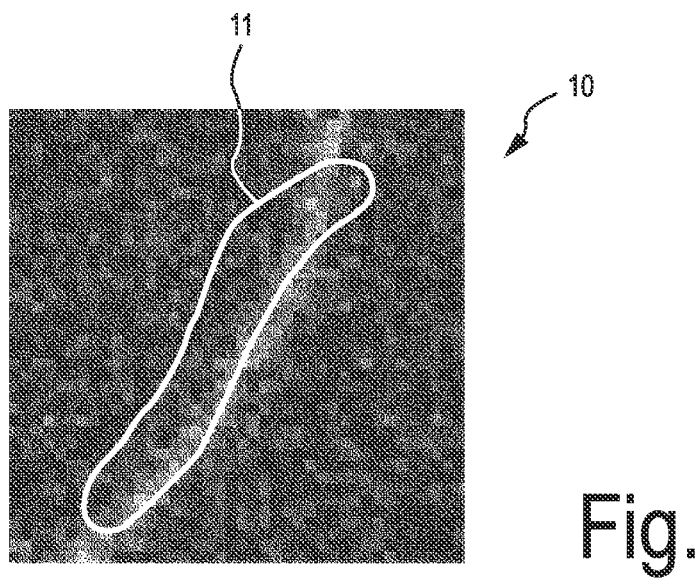
FIG. 3B is a schematic illustration showing an atlas which is registered to the volumetric data according to the exemplary method, which is illustrated in FIG. 2.

By way of example, the data processing system is configured to use segmentation data, which was read and/or generated by the data processing system and to determine the estimate for the longitudinal axis depending on the segmentation data. The segmentation data indicates, for each of a plurality of voxels of the volumetric data, an estimate whether the respective voxel represents a part of the anatomical structure. Therefore, the segmentation data may include a voxel object. In FIG. 3B, the segmentation data are schematically indicated by a white contour 11 within the two-dimensional cross section 10 through the volumetric data.

The segmentation data may be generated by the data processing system or by an external computer system. The segmentation data may be generated using an atlas-based segmentation procedure. However, it is also conceivable that, additionally or alternatively, other segmentation procedures than atlas-based segmentation procedures are used. By way of example, it is conceivable that the segmentation data are generated using an artificial neural network. The segmentation procedure may be automatic or semi-automatic (i.e. requiring user intervention).

The atlas may be generated by integrating segmentation data from multiple segmented images. The multiple images may be generated from different individuals. The atlas may thereby represent an average shape atlas.

The atlas may be registered with at least a portion of diffusion-weighted magnetic resonance data and/or with at least a portion of non-diffusion-weighted magnetic resonance data.

By way of example, the atlas may be registered (in particular directly registered) with magnetic resonance data using a b0 scan (i.e. a non-diffusion weighted scan). The b0 scan may be part of a diffusion tensor imaging data set. The volumetric image data may include the diffusion tensor imaging data set or the volumetric image data may be generated based on the diffusion tensor imaging data set.

Alternatively, it is also conceivable that the atlas is indirectly registered with the diffusion-weighted magnetic resonance data. By way of example, the atlas may be registered to anatomical magnetic resonance data which in turn is registered with the diffusion-weighted magnetic resonance data.

Examples for anatomical magnetic resonance data are but are not limited to: T1 and T2-weighted magnetic resonance data and Constructive Interference in Steady State (CISS) data.

In FIG. 3B, the segmentation data are schematically illustrated as a white contour line 12 in the cross-section 10 through the volumetric data. As can be seen from FIG. 3B, the extent of the anatomical structure, which is derived using atlas registration, is significantly different from the extent of the anatomical structure, as suggested by the levels of fractional anisotropy. However, it has been shown by the inventors that the procedure, which is described in detail in the following, generates an estimate for the extent of the anatomical structure, which is more consistent with the diffusion tensor imaging data.

Figure 4:
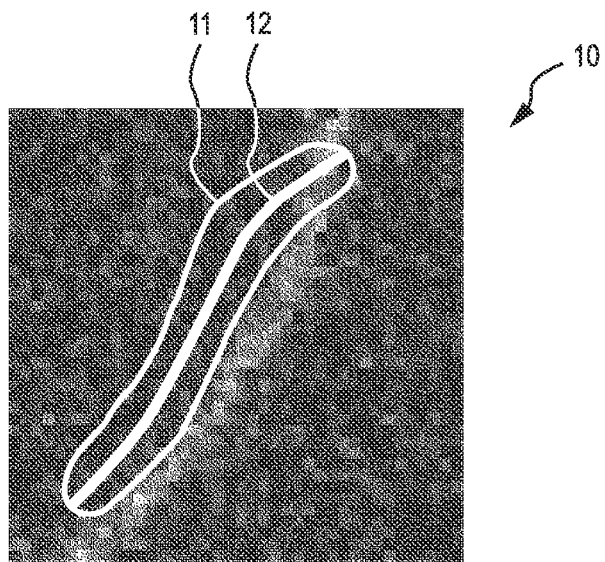
FIG. 4 is a schematic illustration of the determination of an estimate for the longitudinal axis in the exemplary method, which is illustrated in FIG. 2.

As is schematically illustrated in FIG. 4, the data processing system may be configured to generate, depending on the segmentation data 11, the estimate 12 for the longitudinal axis.

Byway of example, determination of the estimate for the longitudinal axis may include successively removing outer layers of the voxel object until a line-shaped object is obtained having a diameter of less than five voxels, or substantially one voxel. Additionally or alternatively, the determination of the estimate for the longitudinal axis may include determining a spline curve representing the estimate for the longitudinal axis. However, it is noted that the present disclosure is not limited to one or a combination of these procedures of determining the longitudinal axis.

Figure 5A:
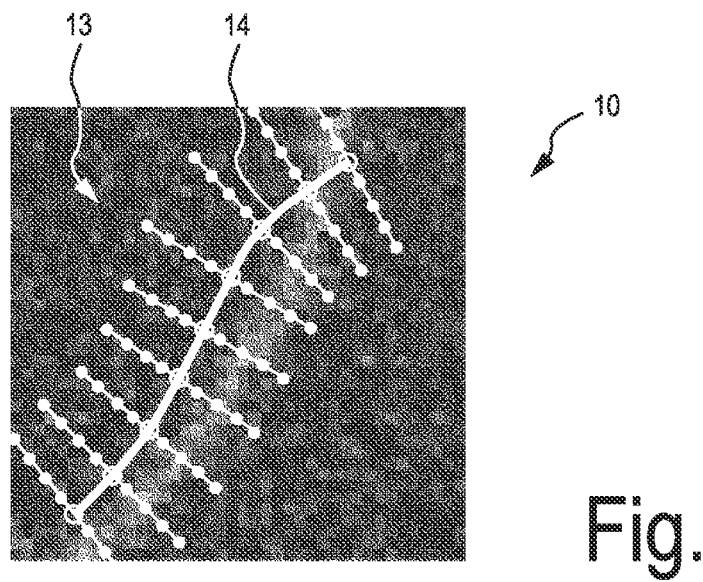
FIG. 5A and FIG. 5B schematically illustrate a deformable template which is used in the exemplary method, which is illustrated in FIG. 2.

As is indicated in FIG. 2, the data processing system is configured to generate S103 a deformable template. Specifically, as is illustrated in FIG. 5A, the data processing system is configured either to use the estimate for the longitudinal axis 12 as a prototype 14 for the deformable template 13 or to generate the prototype 14 based on the estimate for the longitudinal axis 12 (e.g. by approximating the estimate as a polygonal chain). The deformable template 13 is configured as a parametric deformable template representing a set of deformed curves, which are uniquely described by values of a set of parameters. In other words, the geometrical shape, position and/or orientation of the curves of the deformable template 13 can be changed by using different parameter values. The prototype 14 describes only one of the plurality of curves represented by the deformable template 13.

Figure 5B:
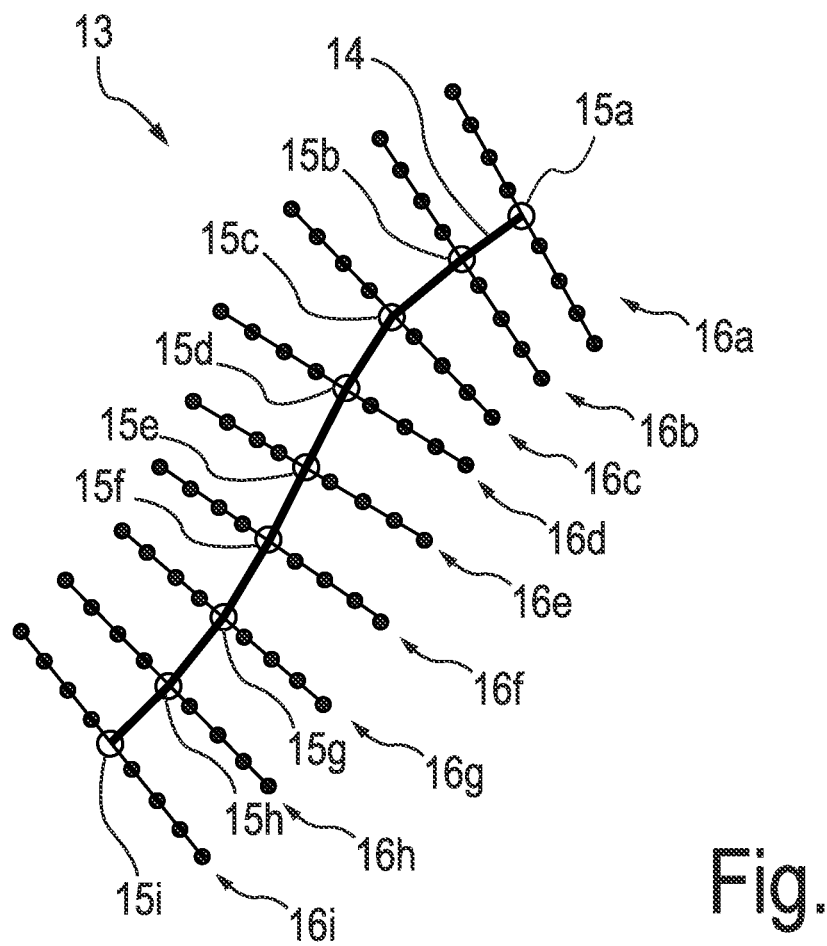

FIG. 5B schematically illustrates the deformable template 13 in more detail. The deformable template 13 includes a plurality of position adjustable control points 15a, ... 15i, (shown as circles in FIG. 5B), which are connected by line segments so that each of the line segments connects two of the position adjustable control points 15a, ... 15i. The line segments which are shown in FIG. 5B together form the prototype 14. By way of example, the data processing system determines the locations of the position adjustable control points 15a, ... 15i of the prototype 14 so that a distance between neighboring position adjustable control points is substantially constant.

Each of the position adjustable control points, 15a, ... 15i, is adjustable within a discrete search space 16a, ... 16i, having a plurality of search space points (indicated in FIG. 5B as black dots) so that separate search spaces are provide for each of the position adjustable control points 15a, ... 15i. In the example, which is shown in FIG. 5B, the search spaces are mutually non-overlapping. Hover, it is also conceivable that at least a portion of the search spaces are overlapping, such as in the exemplary embodiment, which is described further below in connection with FIG. 9.

Figure 6A:
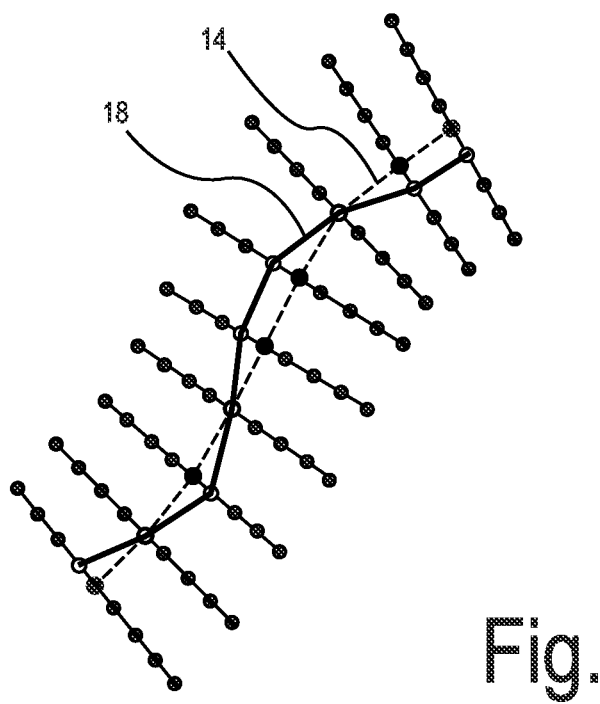
FIG. 6A and FIG. 6B schematically illustrate different curves generated using the deformable template in the exemplary method, which is illustrated in FIG. 2.
Figure 6B:
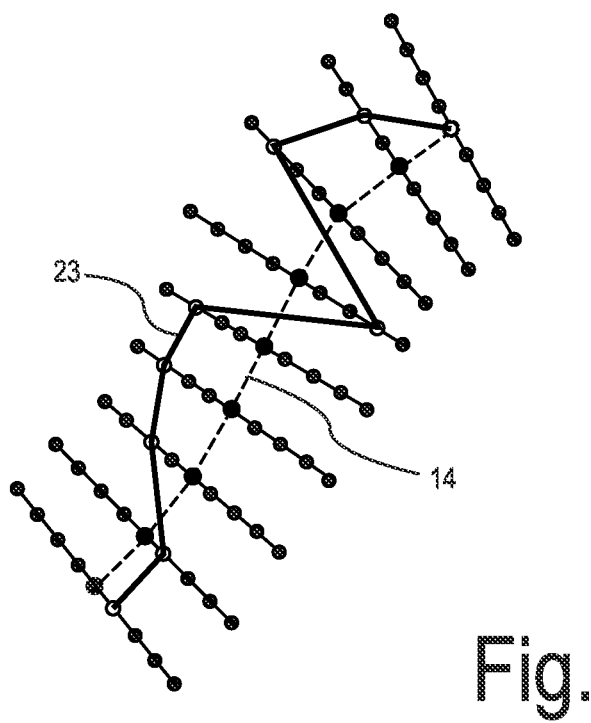

Therefore, the positions of the position adjustable control points within their respective search spaces represent the set of parameters, which defines the shape of the curves represented by the deformable template. Thereby, different positions of the control points within their respective search spaces generate different curves, as is schematically illustrated in FIGS. 6A and 6B.

However, it is noted that the present disclosure is not limited to deformable templates having a polygonal chain. By way of example, the curve may be a spline curve having a degree greater than 1. A spline curve of degree 1 is a polygonal chain. Additionally or alternatively, it is also conceivable that the deformable template having a Bezier curve and/or a NURBS (non-uniform raional B-spline) curve.

For the sake of easy understanding, in the schematic illustration of FIG. 5B, the search space points, which are part of a common search space, are connected by a line. In the illustrated exemplary embodiment, the deformable template is configured so that each of the discrete search spaces 16a, ... 16i forms a plane surface, which is oriented perpendicular to a tangent to the prototype 14 at a location of one of the position adjustable control points of the prototype 14. By way of example, the surfaces which are spanned by the search space points of a discrete search space may be in the form of a disk. It is, however, conceivable that the discrete search spaces have different shapes and/or have a non-planar geometry.

As is further indicated in the flowchart of FIG. 2, the processing system is configured to match S104 the deformable template to the volumetric data in order to obtain a matched template. The matched template is a curve of the deformable template, which optimizes (i.e. maximizes or minimizes) an objective function. The inventors have shown that through such a matching process, a curve can be identified, which represents an estimate for the location of the longitudinal axis of the anatomical structure.

FIGS. 6A and 6B show two curves of the deformable template, which are generated using different sets of parameter values. The curve 18, which is shown in FIG. 6A has a higher degree of smoothness compared to the curve 23, which is shown in FIG. 6B. Further, as measured within the search space of each of the control points, a predominant portion of the control points of the curve 18 of FIG. 6 have a smaller distance from the prototype 14 than the corresponding control points of the deformed template of FIG. 6B. It has been shown that a more reliable estimate for the longitudinal axis of the anatomical structure can be obtained if the matching process favors deformed templates having a smooth appearance and which are located at a small distance from the prototype 14. As will be discussed in the following, this is achieved by the objective function of the deformable template, which is optimized during the matching process.

In the exemplary embodiment, the matching process includes maximizing an objective function, which is the sum of an internal energy function and an external energy function:

$$OF = E_{int} + E_{ext}$$

For each of the curves generated by the deformable template, the internal energy function depends on one or more intrinsic geometric parameters of the respective curve and further on one or more parameters indicative of a distance of the curve from the prototype. The internal energy function is independent from the volumetric data.

In the exemplary embodiment, the internal energy function $E_{int}$ is defined as:

$$E_{int} = E_{dist} + E_{bend},$$

with $E_{dist}$ being the distance energy function, which penalizes large distances from the prototype and $E_{bend}$ being the bending energy, which penalizes sharp bends.

By way of example, the distance energy $E_{dist}$, may be expressed as:

$$E_{dist} = a_{int} \log \prod_{i=1}^{N} \exp\left(\frac{d_i^2}{\sigma^2}\right) = \sum_{i=1}^{N} \frac{d_i^2}{\sigma^2};$$

with N being the number of control points, $d_i$ being the distance of the i-th control point from the corresponding control point position of the prototype. $\sigma$ is a parameter, the value of which determines the degree to which small distances are penalized. The factor $a_{int}$ is a weighting factor that weights the relative contribution of the distance energy $E_{dist}$ to the internal energy $E_{int}$.

Further by way of example, the bending energy $E_{bend}$ may be expressed as:

$$E_{bend} = a_{bend} \sum_{i=1}^{N-1} f(\theta_i)$$

wherein $\theta_i$ is an angle of the i-th segment (which connects the i-th control point with the i+1-th control point) relative to the plane-shaped discrete search space of the i-control point. In an alternative embodiment, the angle $\theta_i$ is the angle between the i-th segment and the i+1-th segment. $f(\theta_i)$ is a function, which penalizes large angles. By way of example, if $\theta_i$ is larger than 35 degrees, the function is not admitted as a candidate for the matched template (e.g. by setting $f(\theta_i)$ to minus infinity). If $\theta_i$ is smaller than 35 degrees, the curve is not penalized (e.g. by setting $f(\theta_i)$ to a constant value of 0). The factor $a_{bend}$ is a weighting factor that weights the relative contribution of the bending energy $E_{bend}$ to the internal energy $E_{int}$.

As such, the internal energy $E_{int}$ penalizes a low degree of smoothness as well as large distances from the prototype.

It is to be noted that the present disclosure is not limited to the above expressions for $E_{int}$, $E_{dist}$ and $E_{bend}$. Various modifications are conceivable regarding the functional form of the internal energy $E_{int}$.

The external energy function, on the other hand, depends on values of the volumetric data. The external energy function depends on an orientation probability density function of an orientation of the longitudinal axis of the anatomical structure. The orientation probability density function is determined for each of a plurality of voxels based on the diffusion tensor data at the respective voxel. At each of the position adjustable control points of a curve, the orientation probability density function is evaluated using one of the adjacent line segments. Specifically, the external energy $E_{ext}$ is calculated as:

$$E_{ext} = \log \prod_{i=1}^{N-1} p(D_i|t_i) = \sum_{i=1}^{N-1} \log(D_i|t_i),$$

wherein $t_i$ represents a line segment of the curve which connects the i-th control point with the i+1-th control point, N is the number of control points and $D_i$ is the diffusion tensor at the ith control point. Therefore, $t_i$ represents a tangent to the curve at the i-th control point. The function $p(D_i|t_i)$ is the orientation probability density function, which indicates, for the direction of $t_i$ at the position of the i-th control point, a probability value that the longitudinal axis of the anatomical structure is oriented along the direction. In exemplary embodiments, in which the curve is not a polygonal chain, $t_i$ represents a tangent to the respective curve at the i-th control point. Therefore, determining the external energy function for a curve of the deformable template may include evaluating, for each of a number of points, the orientation probability density function at the respective point. The orientation probability density function may be evaluated for a direction, which corresponds to a tangent of the curve at the respective point.

It is to be noted that the present disclosure is not limited to a specific functional form of the orientation probability density function. An example for an orientation probability density function is disclosed in the article "Modelling noise-induced fiber orientation error in diffusion-tensor MRI", written by Philip Cook et al. and published in "2004 2nd IEEE International Symposium on Biomedical Imaging: Nano to Macro (IEEE Cat No. 04EX821)", which is incorporated by reference herein in its entirety. This article introduces an orientation probability density function using the Watson Distribution on a sphere. A further example for an orientation probability density function is disclosed in the article "ConTrack: Finding the most likely pathways between brain regions using diffusion tractography", written by Anthony J. Sherbondy et al. and published in the "Journal of Vision (2008) 8 (9): 15, pages 1 to 16, which is incorporated by reference herein in its entirety. This article proposes using a Bingham distribution for determining the orientation probability density function.

In exemplary embodiments, in which the volumetric data are generated using diffusion spectrum imaging (DSI), the determination of the orientation probability density function may include determining an inverse 3D-Fourier transformation based on the diffusion-weighted volumetric images acquired at the sampled q-space points. Further, in exemplary embodiments, in which the volumetric data are generated using single shell or multi-shell high angular resolution imaging (HARDI), the determining of the orientation probability density function may include using a Funk-Radon transform. One of such techniques is termed q-ball imaging and described in the article "Q-Ball Imaging", written by David S. Tuch and published in "Magnetic Resonance in Medicine" 52:1358-1372 (2004), the contents of which is incorporated by reference herein in its entirety.

Figure 7:
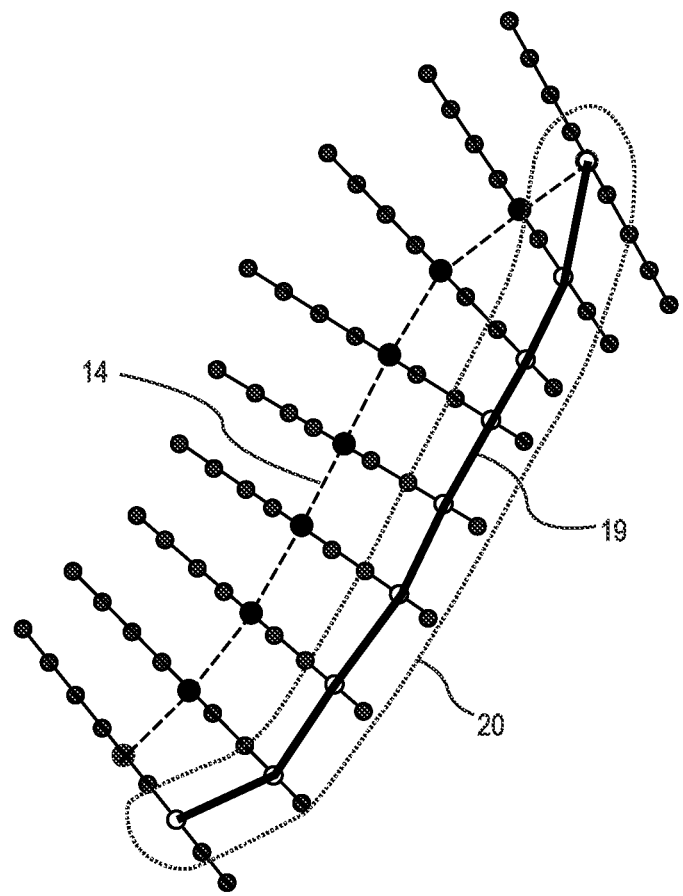
FIG. 7 schematically illustrates a matched template and an estimate for an extent of the anatomical structure, which are determined in the exemplary method, which is illustrated in FIG. 2.

In the exemplary embodiment, the curve, which maximizes the objective function is determined using an exhaustive search. A further, computationally efficient method for determining the matched template is described further below in connection with FIG. 9. FIG. 7 shows a matched template 19, which is a curve of the deformable template, which is obtained by optimizing the objective function. As can be seen from FIG. 7, the total energy function results in a matched template, which has no sharp bends. The matched template 19 represents an approximation for the longitudinal axis of the anatomical structure. Therefore, through the matching process, the data processing system has determined S105 (shown in FIG. 2) position and orientation parameters of the longitudinal axis of the anatomical structure.

The data processing system uses the matched template 19 to determine an extent 20 of the anatomical structure, as it is schematically illustrated in FIG. 7. In order to determine the extent 20 of the anatomical structure, the data processing system uses prior knowledge about the diameter of the anatomical structure (e.g. the diameter of the cranial nerve). Specifically, the data processing system determines a surface, which surrounds the matched template 19 and which is located at a radius from the matched template 19, which corresponds to half of the known diameter of the anatomical structure. Furthermore, also a known length of the anatomical structure can be used to adapt the matched template 19. By way of example, one or both ends of the anatomical structure may be known. Specifically, it is known that all cranial nerves originate from the brain stem. If the shape of the search space of the first control point does not correspond to the shape of the brain stem, this can be corrected by adjusting the length of the matched template.

Figure 8:
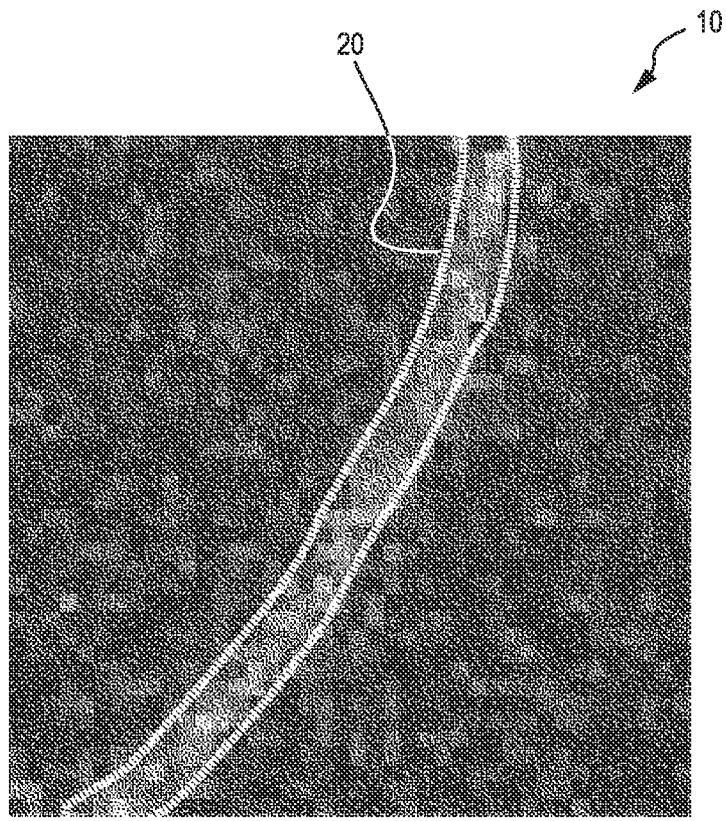
FIG. 8 schematically illustrates a comparison between the volumetric data and the determined estimate for the extent of the anatomical structure which is determined using the exemplary method, which is illustrated in FIG. 2.

FIG. 8 is a comparison between the determined extent 20 and the fractional anisotropy data in the cross-section 10 through the volumetric data. It can be seen from this comparison that the extent 20 which is determined based on the deformable template matches the extent as indicated by the fractional anisotropy levels to a high degree.

Figure 9:
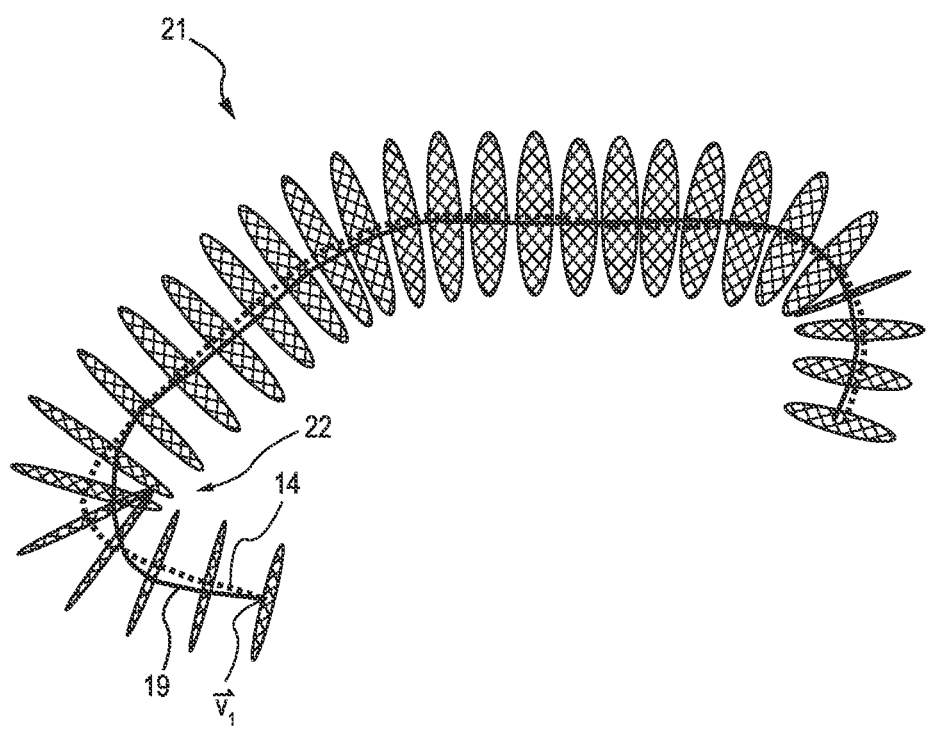
FIG. 9 schematically illustrates a second example of a deformable template which is used by the imaging system in a second exemplary method.

FIG. 9 is a schematic illustration of a deformable template 21, which includes a comparatively high number of position adjustable control points. Due to the high number of discrete search spaces, the total number of curves defined by these search spaces is quite high. However, as is explained in the following, the inventors have shown that it is possible to determine the matched template 19 with a comparatively low computational effort.

Specifically, the inventors have shown, that a computationally efficient determination of the matched template is possible using an objective function (OF), which is expressed as a sum of subfunctions $\psi$:

$$OF(\vec{v_1}, \ldots, \vec{v_N}) = \sum_{k=1}^{N-1} \psi(\vec{v_k}, \vec{v_{k+1}}),$$

with $v_1, \ldots v_N$ being the control point positions and N being the number of control points. Each of the subfunctions $\psi$ depends on control point positions of a neighboring pair of the control points (i.e. a directly consecutive pair, as seen along the longitudinal axis), which are connected by a line segment of the curve and is independent from the positions of the remaining control points of the deformable template. It is noted that the objective function, which was discussed above in connection with the deformable template shown in FIG. 5 fulfills this requirement.

As is explained in the following, the above form of the objective function OF allows determination of the matched template by successively optimizing partial objective functions $POF_j$, for values of j=1 to N−1 (N being the number of control points):

$$POF_j = \sum_{k=1}^{j} \psi(\vec{v_k}, \vec{v_{k+1}}),$$

wherein the optimization is processed in order from j=1 to N−1 and $\vec{v_1}$ (shown in FIG. 9) is a given position of the first control point within its search space and may correspond to the first control point of the prototype 14.

Specifically, for a curve, which starts at the given location of $\vec{v_1}$ of the first control point, for each search space point in the search space of the second control point $\vec{v_2}$, the energy for the curve section between the first and the second control point can be expressed as:

$$POF_1 = \psi(\vec{v_1}, \vec{v_2}),$$

i.e. the energy is determined using the subfunction, which corresponds to the curve section.

As a next step, using the energy values assigned to the search space points within the search space of the second control point, the data processing system identifies, for each search space point in the discrete search space of the third control point, a search space point of the second control point, which maximizes the partial objective function $POF_2$ using the given control point position $\vec{v_1}$ of the first control point. Thereby, an optimized energy value and a corresponding optimized curve section can be assigned to each search space point in the discrete search space of the third control point.

In other words, the optimized energy value is determined using a sum of the subfunctions (i.e. $POF_2$), which correspond to the curve sections.

Then, as a further step, using the energy values assigned to the search space points within the search space of the third control point, the data processing system identifies, for each search space point in the discrete search space of the fourth control point, a search space point within the search space of the third control point, which maximizes the partial objective function $POF_3$ using the optimized energy values assigned to the search space points of the third control point. Thereby, an optimized energy value and a corresponding optimized section of a curve can be assigned to each search space point in the discrete search space of the fourth control point.

In other words, for each of the search space points of the fourth control point, the optimized energy value is determined based on the optimized energy value determined for the third control point and further based on the subfunction $\psi(\vec{v_3}, \vec{v_4})$ which depends on the locations of the third and fourth control point.

Using this procedure, it is possible to determine, for each search space point in the discrete search space of the last (i.e. N-th) control point, an optimized energy value and a curve, which starts at $\vec{v_1}$ and which ends at the respective point in the discrete search space of the last control point.

The data processing system then determines the point in the discrete search space of the last control point, which maximizes the objective function. The corresponding curve 19 (shown in FIG. 9) is then determined to be the matched template.

As can further be seen from the deformable template which is illustrated in FIG. 9, a portion of the discrete search spaces overlap. The overlapping search spaces can lead to curves having a high bending energy, since the curve may change its direction by almost 180 degrees. The matching algorithm can be configured to rearrange for such curves the order of the search spaces in order to avoid sharp bends.

Figure 10:
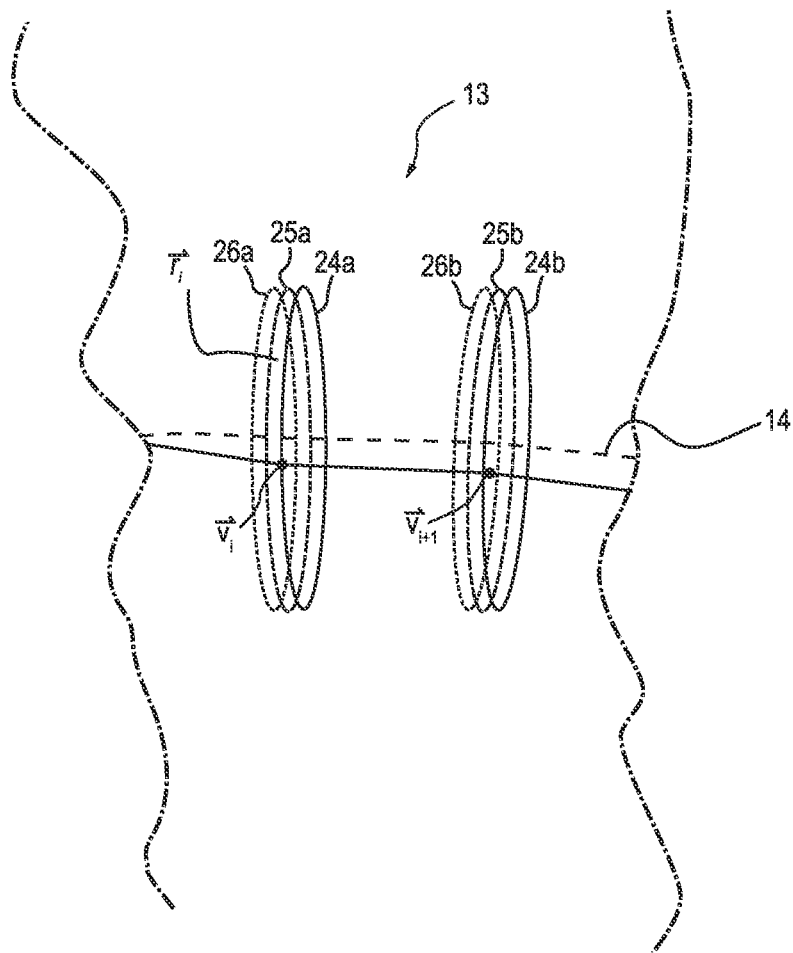
FIG. 10 schematically illustrates a third example of a deformable template which is used by the data processing system in a third exemplary method.

FIG. 10 is a schematic illustration of a portion of a third example of a deformable template 13 which is used by the data processing system in third exemplary method for determining the longitudinal axis of a tubular anatomical structure, such as a vascular body (e.g. a blood vessel).

As is explained in the following in detail, the deformable template 13 according to the third example is configured not only to determine an estimate for the longitudinal axis of the anatomical structure but also to determine, for each control point position of the matched template, an estimate for the radius of the anatomical structure.

The volumetric data based on which the matched template is determined may be anatomical MRT data, such as T1 and/or T2 images. Additionally or alternatively, it is conceivable that one or a combination of the following data acquisition techniques are used: diffusion-weighted magnetic resonance imaging (e.g. using values of fractional anisotropy determined from values of the diffusion tensor), computed tomography, sonography, ultrasound imaging, and positron emission tomography. The volumetric data may represent a three-dimensional scalar field.

In the method according to the third example, the internal energy is the same as mentioned above in connection with the method according to the first example.

As is illustrated in FIG. 10, in the method according to the third example, the deformable template 13 is configured so that for each control point (such as the control points at locations $\vec{v_i}$ and $\vec{v_{i+1}}$ shown in FIG. 10), there are a plurality of search spaces provided (such as the search spaces 24a, 25a and 26a for the control point located at $\vec{v_i}$ and the search spaces 24b, 25b and 26b for the control point located at $\vec{v_{i+1}}$).

For a given control point, each of the search spaces corresponds to a different radius value. By way of example, each of the search spaces 24a and 24b corresponds to a first radius value $R_1$, each of the search spaces 25a and 25b corresponds to second radius value $R_2$ and each of the search spaces 26a and 26b correspond to a third radius value $R_3$.

For the sake of easy illustration, in FIG. 10, the search spaces which are associated to a same control point are illustrated as being partially overlapping. However, in the deformable template 13 of the third example, at each location of a search point (such as the search point location $\vec{r_i}$ which is shown in FIG. 10), there are points of three search spaces located, wherein each of the search spaces corresponds to a different radius value ($R_1$, $R_2$, $R_3$).

The deformable template 13 is configured to determine an estimate for an extent of the anatomical structure by providing an estimate for the longitudinal axis and estimates for radius values at a plurality of locations along the longitudinal axis. The radius values are limited to discrete values, such as the three values $R_1$, $R_2$, $R_3$. It is noted in this regard that the number of radius values (and therefore the number of search spaces for each control point) may be greater than three or less than three. The number may be chosen depending on the anatomical structure, which is analyzed and/or depending on the required accuracy. The number of discrete radius values (and therefore the number of search spaces) as well as the values for the radii may be identical for each control point of the deformable template or may be different among the control points.

In the method according to the third example, the data processing system determines for each of the search space points of a control point (i.e. for each of the search points in the plurality of search spaces which are associated with different radius values), a probability measure P which is a measure for the probability that the longitudinal axis passes through the respective search space point and has a radius value which is assigned to the respective search space point.

The probability measure P may be determined using a Gradient Vector Flow vector field which is determined using the volumetric data and by solving a partial differential equation. The vectors of the Gradient Vector Flow vector field point to object edges of the anatomical structure. However, it is also conceivable that the values of the probability measure P are determined using the gradient vector field which is determined based on the volumetric data.

Specifically, using the Gradient Vector Flow field, the probability measure P may be determined for the search space point located at a location $\vec{r_i}$ as follows: an estimate for a cross-sectional plane is determined which passes through $\vec{r_i}$ and which is approximately located perpendicular to the longitudinal axis. The estimate for the cross-sectional plane may be determined using a least squares fitting method based on the Gradient Vector Flow field. Additionally or alternatively, the estimate for the cross-sectional plane may be determined using the prototype for the deformable template. By way of example, the cross-sectional plane may be determined so that it passes through $\vec{r_i}$ and is oriented perpendicular to a tangent to the prototype.

Using the estimated cross-sectional plane, for each of the three search space points at the location $\vec{r_i}$ (i.e. the search space point for the search space 24a, the search space point for the search space 24b and the search space point for the search space 24c), the probability measure P is determined using the flux of the Gradient Vector Flow field (or the gradient vector field) which is projected onto the cross-sectional plane and which passes through a circle having the radius of the respective search space point (i.e. the radius value $R_1$, $R_2$ or $R_3$).

The external energy $E_{ext}$ for a curve of the deformable template is then expressed using the determined values for the probability measure P. Specifically, a curve which is defined by the control points location $\vec{v_i} \ldots \vec{v_N}$ and which has the radius values $\hat{R_1} \ldots \hat{R_N}$ at the respective control point locations ($\hat{R_i}$ being one of $R_1$, $R_2$ or $R_3$), the external energy is expressed as:

$$E_{ext} = \Sigma_{i=1}^{N} P(\vec{r_i}, \hat{R_i}),$$

with N being the number of control points. Therefore, the external energy function is a function of the locations of the control points and further a function of a radius value for each of the control points.

Therefore, in a similar manner as has been described in connection with the method according to the second example, the objective function can be expressed as a sum of subfunctions:

$$OF(\vec{v_1}, \ldots, \vec{v_N}, \widehat{R_1}, \ldots \widehat{R_N}) = \Sigma_{k=1}^{N-1} \psi(\vec{v_k}, \vec{v_{k+1}}, \widehat{R_k}, \widehat{R_{k+1}}),$$

that the process of matching the deformable template to the volumetric data can be carried out in a similar manner as has been described above in connection with the method according to the second example.

In other words, each of the subfunctions depends on two radius values, each of which representing a radius of the anatomical structure at one of the consecutive control points.

Specifically, as is explained in the following, the above form of the objective function OF allows determination of the matched template by successively optimizing partial objective functions $POF_j$, for values of j=1 to N−1 (N being the number of control points):

$$POF_j = \Sigma_{k=1}^{j} \psi(\vec{v_k}, \vec{v_{k+1}}, \widehat{R_k}, \widehat{R_{k+1}}),$$

wherein the optimization is processed in order from j=1 to N−1 and $\vec{v_1}$ is a given position of the first control point within its search spaces and may correspond to the first control point of the prototype 14.

For each search space point in the search spaces of the second control point $\vec{v_2}$, (i.e. for each location and radius value), the energy for the curve section between the first and the second control point can be expressed as:

$$POF_1 = \psi(\vec{v_1}, \vec{v_2}, \widehat{R_1}, \widehat{R_2}),$$

wherein $\vec{v_1}$ is the given position of the first control point within its search space and the Radius value $\widehat{R_1}$ can be obtained by optimizing the external energy function which corresponds to the curve section (i.e. $E_{ext} = P(\vec{r_1}, \widehat{R_1}) + P(\vec{r_2}, \widehat{R_2})$), As a next step, using the energy values assigned to the search space points of the second control point, the data processing system identifies, for each search space point of the third control point, a search space point (i.e. a location and a radius value) of the second control point, which maximizes the partial objective function $POF_2$ using the given control point position $\vec{v_1}$ and the given radius value $\widehat{R_1}$ of the first control point. Thereby, an optimized energy value and a corresponding optimized curve section (including the radius values at the control points of the optimized curve section) can be assigned to each search space point of the third control point.

Then, as further step, using the energy values assigned to the search space points of the third control point, the data processing system identifies, for each search space point of the fourth control point, a search space point (i.e. a location and a radius value) of the third control point, which maximizes the partial objective function $POF_3$ using the optimized energy values assigned to the search space points of the third control point. Thereby, an optimized energy value and a corresponding optimized curve section (including the radius values at the control points of the optimized curve section) can be assigned to each search space point of the fourth control point.

Using this procedure, it is possible to determine, for each search space point in the discrete search spaces of the last (i.e. N-th) control point, an optimized energy value and an optimized curve (including the radius value at each control point of the optimized curve), which starts at $\vec{v_1}$ and which ends at the respective search space point of the last control point.

The data processing system then determines the search space point in the search spaces of the last control point, which maximizes the objective function OF. The corresponding curve, including the radius values for each control points of the curve is then determined to be the matched template.

Thereby, a computationally efficient process is provided for determining the extent of the anatomical structure.

We claim:

1. A computer-implemented method of determining one or more position and/or orientation parameters of an anatomical structure of a body portion, wherein the anatomical structure has a longitudinal shape defining a longitudinal axis;
wherein the method comprises:
generating and/or reading, by a data processing system, volumetric data of at least a portion of a subject;
generating, by the data processing system, a deformable template which provides an estimate for a location of the longitudinal axis in the portion of the subject;
matching, by the data processing system, the deformable template to the volumetric data, thereby obtaining a matched template;
wherein the matching comprises using one or more internal energy functions and one or more external energy functions for optimizing an objective function; and
determining, by the data processing system, the one or more position and/or orientation parameter based on the matched template;
wherein the deformable template represents a plurality of curves and wherein each of the plurality of curves is at least partially defined using a plurality of position adjustable control points.

2. The method of claim 1, wherein the deformable template comprises, for each of the control points, a discrete search space having a plurality of search space points for positioning the adjustable control points.

3. The method of claim 2, wherein for at least a portion of the control points, the search spaces of the control points are mutually non-overlapping.

4. The method of claim 2, wherein for one or more of the control points, the plurality of search space points for the respective control point form a plane or curved surface.

5. The method of claim 1, further comprising:
registering an atlas with the volumetric data; and
determining a prototype of the deformable template based on the registered atlas.

6. The method of claim 1, further comprising determining, for each of a plurality of voxels, one or more values of an orientation probability density function of an orientation of the longitudinal axis at the respective voxel.

7. The method of claim 1, wherein each of the plurality of curves is an approximation for the longitudinal axis.

8. The method of claim 1, wherein at least one of the one or more internal energy functions depends on a distance of one or more control points of the deformable template from a prototype of the deformable template.

9. The method of claim 1, wherein at least one of the one or more external energy functions is a function of the locations of the control points and further a function of radius values of the anatomical structure at the locations.

10. The method of claim 1, wherein the objective function comprises a sum of subfunctions, which depends on all control points,
wherein each of the subfunctions:
depends on positions of directly consecutive control points, as seen along the curve; and
is independent from the remaining control points.

11. The method of claim 10, further comprising:
determining, for each search space point of a first one of the control points, an optimized energy value based on sections of the plurality of curves, which end at the respective search space point;
wherein the optimized energy value is determined using one or a sum of the subfunctions, which corresponds to the curve sections.

12. The method of any one of claim 1, wherein for one or more of the plurality of curves, at least a portion of the respective curve is a polygonal chain having a plurality of line segments, each of which connecting two of the position adjustable control points.

13. The method of claim 12, wherein for one or more of the control points, the plurality of search space points for the respective control point form a plane or curved surface; and
at least one of the one or more internal energy functions is a function of an angle formed between a line segment of the polygonal chain and one of the surfaces.

14. The method of claim 12, wherein at least one of the one or more internal energy functions is a function of an angle formed between two neighboring line segments of the polygonal chain.

15. The method of claim 1, wherein the volumetric data comprise directional diffusion data for each of a plurality of voxels of the volumetric data.

16. The method of claim 1, wherein for each of a plurality of voxels of the volumetric data, the volumetric data are indicative of a directional anisotropy of an apparent diffusion coefficient at the respective voxel.

17. The method of claim 1, wherein the volumetric data comprise: a diffusion tensor for each of a plurality of voxels of the volumetric data.

18. The method of claim 1, wherein the volumetric data comprise a plurality of diffusion-weighted volumetric images, each of which being acquired at a different point in q-space.

19. A non-transitory computer readable media comprising instructions for determining one or more position and/or orientation parameters of an anatomical structure of a body portion, wherein the anatomical structure has a longitudinal shape defining a longitudinal axis, which, when executed by at least one processor, causes the at least one processor to:
generate and/or read, by the at least one processor, volumetric data of at least a portion of a subject;
generate, by the at least one processor, a deformable template which provides an estimate for a location of the longitudinal axis in the portion of the subject;
match, by the at least one processor, the deformable template to the volumetric data, thereby obtaining a matched template;
wherein the matching comprises using one or more internal energy functions and one or more external energy functions for optimizing an objective function; and
determine, by the at least one processor, the one or more position and/or orientation parameter based on the matched template;
wherein the deformable template represents a plurality of curves and wherein each of the plurality of curves is at least partially defined using a plurality of position adjustable control points.

20. A system for determining one or more position and/or orientation parameters of an anatomical structure of a body portion, wherein the anatomical structure has a longitudinal shape defining a longitudinal axis; comprising:
a radiation treatment apparatus comprising a treatment beam source and a patient support unit;
at least one processor executing instructions to:
generate and/or read, by the at least one processor, volumetric data of at least a portion of a subject;
generate, by the at least one processor, a deformable template which provides an estimate for a location of the longitudinal axis in the portion of the subject;
match, by the at least one processor, the deformable template to the volumetric data, thereby obtaining a matched template;
wherein the matching comprises using one or more internal energy functions and one or more external energy functions for optimizing an objective function; and
determine, by the at least one processor, the one or more position and/or orientation parameter based on the matched template;
wherein the deformable template represents a plurality of curves and
wherein each of the plurality of curves is at least partially defined using
a plurality of position adjustable control points.

* * * * *

UNITED STATES PATENT AND TRADEMARK OFFICE
CERTIFICATE OF CORRECTION

PATENT NO. : 11,741,614 B2
APPLICATION NO. : 17/579245
DATED : August 29, 2023
INVENTOR(S) : Rainer Lachner and Katrin Unterlindner It is certified that error appears in the above-identified patent and that said Letters Patent is hereby corrected as shown below:

In the Specification

In Column 3, Line 9, delete "for for" and insert -- for --, therefor.

In Column 15, Line 12, delete "data from data from" and insert -- data from --, therefor.

In Column 19, Line 62, delete "$E_{bend}=a_{bend}\sum_{i=1}^{N-1}f(\theta_i)$" and insert -- $E_{bend} = a_{bend} \sum_{i=1}^{N-1} f(\theta_i)$ --, therefor.

In Column 22, Line 35, delete "$POF_1 = \psi(\overrightarrow{v_1}, \overrightarrow{v_2})),$" and insert -- $POF_1 = \psi(\overrightarrow{v_1}, \overrightarrow{v_2}),$ --, therefor.

In Column 22, Line 67, delete "value" and insert -- values --, therefor.

In Column 23, Line 2, delete "$\psi(\overrightarrow{v_3}, \overrightarrow{v_4})$" and insert -- $\psi(\overrightarrow{v_3}, \overrightarrow{v_4})$ --, therefor.

In Column 24, Line 36, delete "$\overrightarrow{r_i}$" and insert -- $\overrightarrow{r_i}$ --, therefor.

In Column 24, Line 45, delete "$\overrightarrow{r_i}$" and insert -- $\overrightarrow{r_i}$ --, therefor.

Signed and Sealed this
Thirtieth Day of January, 2024

Katherine Kelly Vidal
*Director of the United States Patent and Trademark Office*

CERTIFICATE OF CORRECTION (continued)
U.S. Pat. No. 11,741,614 B2

In Column 25, Line 10, delete "$OF(\vec{v_1}, \ldots, \vec{v_N}, \widehat{R_1}, \ldots, \widehat{R_N}) = \sum_{k=1}^{N-1} \psi(\vec{v_k}, \vec{v_{k+1}}, \widehat{R_k}, \widehat{R_{k+1}}),$" and insert -- $OF(\vec{v_1}, \ldots, \vec{v_N}, \widehat{R_1}, \ldots \widehat{R_N}) = \sum_{k=1}^{N-1} \psi(\vec{v_k}, \vec{v_{k+1}}, \widehat{R_k}, \widehat{R_{k+1}}),$ --, therefor.